United States Patent
Morrell et al.

(10) Patent No.: US 8,114,677 B2
(45) Date of Patent: Feb. 14, 2012

(54) PASSIVE IN-SITU CHEMICAL SENSOR

(75) Inventors: Jonathan S. Morrell, Farragut, TN (US); Edward B. Ripley, Knoxville, TN (US)

(73) Assignee: Babcock & Wilcox Technical Services Y-12, LLC., Oak Ridge, TN (US)

( * ) Notice: Subject to any disclaimer, the term of this patent is extended or adjusted under 35 U.S.C. 154(b) by 599 days.

(21) Appl. No.: 12/243,247

(22) Filed: Oct. 1, 2008

(65) Prior Publication Data

US 2010/0081206 A1    Apr. 1, 2010

(51) Int. Cl.
*G01N 27/00* (2006.01)
*G01N 25/20* (2006.01)

(52) U.S. Cl. ..... 436/147; 436/149; 436/151; 422/82.01; 422/82.12

(58) Field of Classification Search ................... 436/147, 436/149, 151; 422/82.01, 82.12
See application file for complete search history.

(56) References Cited

U.S. PATENT DOCUMENTS

| | | | | |
|---|---|---|---|---|
| 3,878,049 | A | * | 4/1975 | Tannenbaum et al. ..... 205/777.5 |
| 4,685,463 | A | * | 8/1987 | Williams ....................... 600/365 |
| 4,935,345 | A | * | 6/1990 | Guilbeau et al. ................. 435/14 |
| 5,879,630 | A | * | 3/1999 | Lescouzeres et al. ..... 422/82.02 |
| 2005/0076943 | A1 | * | 4/2005 | Cooper et al. ................. 136/224 |

* cited by examiner

*Primary Examiner* — Maureen Wallenhorst
(74) *Attorney, Agent, or Firm* — Michael J. Renner, Esq.; Luedeka, Neely & Graham, P.C.

(57) ABSTRACT

A chemical sensor for assessing a chemical of interest. In typical embodiments the chemical sensor includes a first thermocouple and second thermocouple. A reactive component is typically disposed proximal to the second thermal couple, and is selected to react with the chemical of interest and generate a temperature variation that may be detected by a comparison of a temperature sensed by the second thermocouple compared with a concurrent temperature detected by the first thermocouple. Further disclosed is a method for assessing a chemical of interest and a method for identifying a reaction temperature for a chemical of interest in a system.

20 Claims, 9 Drawing Sheets

FIG. 8

210 — Measuring a first electrical property based on the conditions at a first thermocouple 212 — Exposing a first reactive component to a chemical of interest at a second thermocouple 214 — Measuring a second electrical property based on the conditions at the second thermocouple during a thermal excursion at the second thermocouple caused by a first chemical reaction 216 — Comparing the measurement of the first electrical property with the measurement of the second electrical property value 218 — Identifying the chemical of interest based on calibration data and the comparison of the measurement of the first electrical property with the measurement of the second electrical property

FIG. 9

310 — Measuring a plurality of first electrical property values based on the conditions at a reference location within the system

312 — Exposing a reactive material to a chemical of interest at an experimental location inside the system

314 — Measuring a plurality of second electrical property values based on the conditions at the experimental location within the system

316 — Comparing the measured plurality of first electrical property values with the plurality of second electrical property values

318 — Measuring the temperature of the system adjacent the reference location and the experimental location

320 — Controlling the temperature of the system so that the measured temperature in the system remains substantially unchanged and is therefore known when measurements are taken of the plurality of first electrical property values and the plurality of second electrical property values

PASSIVE IN-SITU CHEMICAL SENSOR

GOVERNMENT RIGHTS

The U.S. Government has rights to this invention pursuant to contract number DE-AC05-00OR22800 between the U.S. Department of Energy and Babcock & Wilcox Technical Services Y-12, LLC.

FIELD

This disclosure relates to the field of detectors for chemicals. More particularly, this disclosure relates to in-situ sensors for detecting, quantifying, and/or analyzing chemicals.

BACKGROUND

In many chemical processes it is often desirable to detect the presence, quantity, and/or qualities of certain chemicals of interest. For example, in many closed chemical processes (either batch or continuous) the generation or infiltration of certain deleterious chemicals can damage or ruin the effectiveness of the process. By continually or periodically monitoring such processes the presence and/or amount of a deleterious chemical may be timely reported and damage to the system may be averted. As another example many systems include a residual or "background" concentration of an undesirable chemical that is acceptable. However, once the background level increases to a certain threshold limit, the higher concentration of the undesirable chemical becomes unacceptable and some action must be taken to avert danger to persons or damage to man-made materials and/or the environment. Accurate and sensitive monitoring techniques are tools that are used for these and similar types of applications.

One difficulty in monitoring certain chemical processes is that such monitoring may in itself have a negative effect on a system being monitored. For example, the presence of a monitoring device may interrupt system flow or adversely affect system output quality. Often, negative effects associated with certain monitoring equipment are due to the size of the monitoring equipment or the requirement of actively interjecting such monitoring equipment into a system from outside the system. Additionally, many chemical monitor devices or monitoring systems are limited in that only the presence of a particular chemical may be indicated as opposed to indicating quantity and/or quality information.

What are needed therefore are chemical sensors that are capable of passively monitoring a particular application in-situ so that the application is substantially unaffected by the presence of the sensor. What are also needed are chemical sensors and/or sensor systems that are capable of generating accurate and detailed quantification information based on differences in temperature gradients over time. What are further needed are in-situ chemical sensors that are capable of indicating a threshold event using an expendable and very small sensing apparatus.

SUMMARY

In one embodiment the present disclosure provides a chemical sensor for assessing a chemical of interest in a system having an operational temperature that varies over a temperature range. The sensor includes a first thermocouple disposed in the system and configured for exhibiting a first electrical property that varies over the temperature range according to a first calibration curve. The sensor further includes a first detector assembly including a second thermocouple and a proximate first reactive component, the first detector assembly disposed adjacent the first thermocouple in the system and wherein the second thermocouple is configured for exhibiting a second electrical property that varies over the temperature range according to a second calibration curve, and wherein the first reactive component undergoes a first chemical reaction correlating to a first maximum temperature property variation if the first reactive component is exposed to a first chemical of interest, and wherein the second electrical property changes according to a temperature change caused by the first chemical reaction. In one embodiment, the first reactive component is attached adjacent a first surface along the second thermocouple and the first detector assembly further includes a second reactive component attached adjacent a second surface along the second thermocouple. In another embodiment, the second thermocouple further includes a selective barrier attached adjacent the second thermocouple such that the first reactive component is substantially prevented from being exposed to chemicals that are substantially incapable of transporting through the selective barrier.

The embodiments described above preferably include a reader configured to compare the first electrical property and the second electrical property, to use the first calibration curve and the second calibration curve to calculate a first maximum temperature property variation between the first thermocouple and the second thermocouple wherein the first maximum temperature property variation varies according to a third calibration curve associated with the chemical of interest, and to use the first maximum temperature property variation between the first thermocouple and the second thermocouple along with the third calibration curve to indicate the presence of the first chemical of interest. The reader is preferably further configured for recording time stamped temperature property data for the first thermocouple and the second thermocouple. In a related embodiment, the reader is further configured for using the time stamped temperature property data to generate first chemical reaction data based on the time stamped temperature property data associated with the first chemical reaction. In yet another related embodiment, the reader is further configured for analyzing the first chemical reaction data according to an analysis program known to a person having ordinary skill in the art and generating output data based on an analysis of the first chemical reaction data.

In a related embodiment, a chemical sensor is disclosed wherein the first reactive component includes a first chemical substance that yields a product when exposed to the chemical of interest during the first chemical reaction and wherein the product reacts with a second chemical substance in the reactive component, defining a second chemical reaction that includes a second maximum temperature property variation, wherein the magnitude of the second maximum temperature property variation is greater than the magnitude of the first maximum temperature property variation.

Another embodiment includes one of the chemical sensors described above wherein the sensor further includes a calibration assembly including a third thermocouple adjacent the first thermocouple and a first non-reactive component proximate the third thermocouple, the third thermocouple configured for generating a third electrical property that varies over the temperature range, wherein the first non-reactive component is selected so as to substantially imitate the heat transfer properties of the first reactive component, wherein the variation of the third electrical property may be compared by the reader to the variation of the first electrical property, and wherein the effect of any difference between the variation of the first electrical property and the variation of the third electrical property may be accounted for during the calculation of the first maximum temperature property variation.

Yet another related embodiment includes one of the chemical sensors described above and further includes a second detector assembly comprising a third thermocouple and a proximate second reactive component, the second detector assembly disposed adjacent the first thermocouple in the system and wherein the third thermocouple is configured for generating a third electrical property that varies over the temperature range according to a third calibration curve, and wherein the second reactive component undergoes a second chemical reaction if the second reactive component is exposed to a second chemical of interest, and wherein the third electrical property changes according to a temperature change induced by the second chemical reaction.

An embodiment of one of the chemical sensors described above may further include a second detector assembly including a third thermocouple and a proximate second reactive component, the second detector assembly disposed adjacent the first thermocouple in the system and wherein the third thermocouple is configured for generating a third electrical property that varies over the temperature range according to a third calibration curve, and wherein the second reactive component undergoes a second chemical reaction if the second reactive component is exposed to a second chemical of interest, and wherein the third electrical property changes according to a temperature change induced by the second chemical reaction, the reader configured to compare the first electrical property and the third electrical property, to use the first calibration curve and the third calibration curve to calculate a second maximum temperature property variation between the first thermocouple and the second thermocouple wherein the second maximum temperature property variation varies according to a fourth calibration curve, and to use the second maximum temperature property variation between the first thermocouple and the third thermocouple along with the fourth calibration curve to indicate the presence of the second chemical of interest.

Another embodiment provides a closed system including an enclosed structure and an embodiment of one of the chemical sensors described above attached to the interior of the enclosed structure.

The disclosure also provides embodiments of a method for assessing a chemical of interest in a system. One embodiment includes the steps of (a) measuring a first electrical property value based on the conditions at a reference location within the system; (b) triggering a first chemical reaction by exposing a reactive material to a chemical of interest at an experimental location inside the system; (c) measuring a second electrical property value based on the conditions at the experimental location within the system; (d) comparing the measurement of the first electrical property value with the measurement of the second electrical property value; and (e) identifying the chemical of interest based on calibration data and the comparison of the measurement of the first electrical property value with the measurement of the second electrical property value.

In a related embodiment, the method described above further includes the steps of (f) recording a plurality of first electrical property values during a first time period $\Delta t_1$; and (g) recording a plurality of second electrical property values during a second time period $\Delta t_2$.

In another related embodiment, the method described above wherein the second time period $\Delta t_2$ is substantially identical to the first time period $\Delta t_1$.

In a related embodiment, the method described above further includes the step of (h) calculating temperature variation deviation data based on a deviation between first temperature variation data associated with the plurality of first electrical property values and second temperature variation data associated with the plurality of second electrical property values, wherein the plurality of first electrical property values are associated with the first temperature variation data based on a first calibration curve, and wherein the plurality of second electrical property values are associated with the second temperature variation data based on a second calibration curve.

In a related embodiment, the method described above further includes the step of (i) calculating quantitative mass data of the chemical of interest based on the generated thermal excursion data and the calculated temperature variation deviation data.

In yet another related embodiment, the method described above further includes the step of (j) estimating the remaining shelf life of an object located in the system based on the calculated quantitative mass data of the chemical of interest and a known relationship between the chemical of interest and the object.

The disclosure also provides embodiments of a method for identifying a reaction temperature for a chemical of interest in a system. The method includes the steps of (a) measuring a plurality of first electrical property values based on the conditions at a reference location within the system; (b) exposing a reactive material to a chemical of interest at an experimental location inside the system; (c) measuring a plurality of second electrical property values based on the conditions at the experimental location within the system; (d) comparing the measured plurality of first electrical property values with the plurality of second electrical property values; (e) measuring the temperature of the system adjacent the reference location and the experimental location; and (f) controlling the temperature of the system so that the measured temperature in the system remains substantially unchanged and is therefore known when measurements are taken of the plurality of first electrical property values and the plurality of second electrical property values.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein:

FIG. 8 shows a diagram of a related embodiment of a method for detecting, quantifying, and/or analyzing a chemical of interest; and FIG. 9 shows a diagram of an embodiment of a method for determining a reaction temperature of a chemical of interest.

DETAILED DESCRIPTION

In the following detailed description of the preferred embodiments, reference is made to the accompanying drawings, which form a part hereof, and within which are shown by way of illustration the practice of specific embodiments of chemical detection sensors and systems. It is to be understood that other embodiments may be utilized, and that structural changes may be made and processes may vary in other embodiments.

Figure 1:
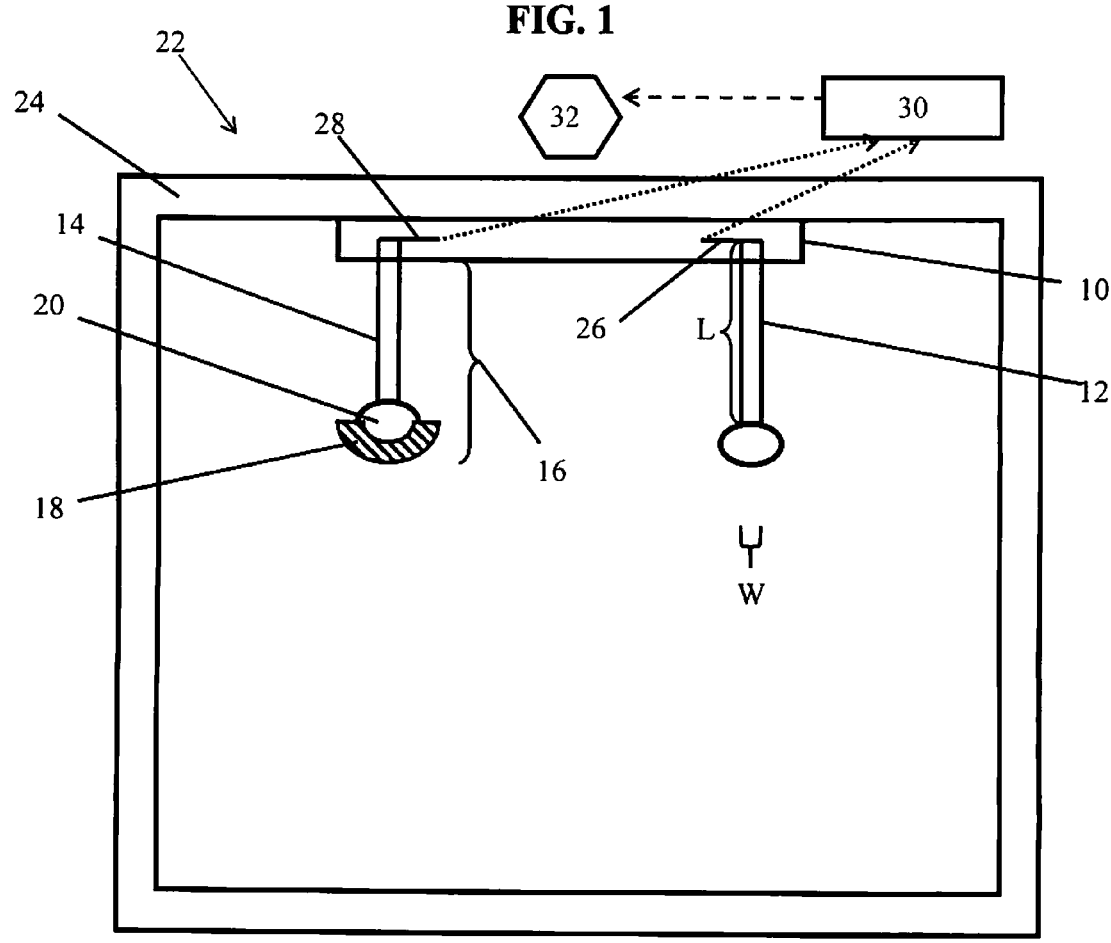
FIG. 1 shows a somewhat schematic side view of an embodiment of a chemical sensor in a system.

FIG. 1 illustrates one embodiment of a chemical sensor 10. The sensor 10 includes a reference thermocouple 12 and a first experimental thermocouple 14 adjacent the reference thermocouple 12. The basic functioning and structure of thermocouples are known to a person having ordinary skill in the art, so background information on thermocouple structure and basic function will not be covered in depth here. The first experimental thermocouple 14 forms part of a first detector assembly 16 including both the first experimental thermocouple 14 and a first reactive component 18 attached proximate to the first experimental thermocouple 14 at a first joint 20. In the embodiment shown in FIG. 1, the sensor 10 is located in a closed system 22 defined at least in part by an enclosing structure 24. The sensor 10 is preferably very small so that it does not interfere with any processes or functioning of the system 22. For example, the width of the first experimental thermocouple leads preferably ranges from about $3 \times 10^{-3}$ inches to about $5 \times 10^{-3}$ inches, and most preferably is about $3 \times 10^{-3}$ inches, shown as length "W" in FIG. 1. The preferred small size range also allows for many thermocouples to be present in the system 22 for monitoring, analyzing, and/or detecting various chemicals of interest simultaneously. The width W may be significantly larger in other applications. Additionally, the length "L" of the first experimental thermocouple 14 leads may vary depending on the application. Although the system 22 in FIG. 1 is defined as a closed system, the sensor 10 may also be used in open systems. The sensor 10 is preferably provided in the system 22 in-situ during manufacturing of the system 22.

During sensor 10 operation, the reference thermocouple 12 yields an electrical property, more preferably, a slight voltage variation ($\Delta V_R$) at a first reference location 26 wherein the voltage variation $\Delta V_R$ corresponds to a temperature variation ($\Delta T_R$) according to a first calibration curve. An example of a calibration curve for a Type J thermocouple correlating $\Delta V$ to $\Delta T$ is given by the fifth order polynomial Equation (1) below wherein "T" represents temperature variation in degrees Centigrade, "x" represents voltage variation given in volts, and coefficient values for $a_0$, $a_1$, $a_2$, $a_3$, $a_4$, and $a_5$ are given in Table 1 below.

$$T = a_0 + a_1 x + a_2 x^2 + a_3 x^3 + a_4 x^4 + a_5 x^5 \quad \text{Eq. 1}$$

TABLE 1

| | |
|---|---|
| $a_0$ | −0.048868252 |
| $a_1$ | 19873.14503 |
| $a_2$ | −218614.5353 |
| $a_3$ | 11569199.78 |
| $a_4$ | −264917531.4 |
| $a_5$ | 2018441314 |

Although a Type J thermocouple is given as an example, all types of thermocouples are contemplated by this disclosure including, but not limited to, Type E, Type K, Type R, Type S, and Type T thermocouples.

During operation of the sensor 10, the first experimental thermocouple 14 yields a slight voltage variation ($\Delta V_{E1}$) at a second reference location 28 wherein the voltage variation $\Delta V_{E1}$ corresponds to a temperature variation ($\Delta T_{E1}$) according to a second calibration curve. Preferably, the second calibration curve is substantially identical to the first calibration curve. The first reactive component 18 is selected based on a high likelihood of reaction with a chemical of interest. A "chemical of interest" may include one or more chemical species that may be in any physical form (e.g., solid, liquid, gas, plasma). If a chemical of interest becomes present in the system 22, the first reactive component 18 will react through a first chemical reaction with the chemical of interest. The first chemical reaction is either exothermic or endothermic at some level, thereby causing $\Delta V_{E1}$ to differ from $\Delta V_R$. Thus, $\Delta T_{E1}$ differs from $\Delta T_R$.

The sensor 10 preferably includes a reader 30 for comparing $\Delta V_{E1}$ to $\Delta V_R$. Reader 30 also preferably is capable of generating temperature variation data comparing $\Delta T_{E1}$ to $\Delta T_R$ based on $\Delta V_{E1}$ and $\Delta V_R$ according to the first calibration curve and the second calibration curve. The reader 30 may be in direct contact with the system 22 or, alternatively the reader may be in indirect contact with the system 22 (e.g., a wireless connection). In a preferred embodiment, the reader 30 generates a first maximum temperature variation T1$_{max}$ which is equal to $\Delta T_{E1}$ minus $\Delta T_R$ and which varies according to a third calibration curve associated with the chemical of interest. If T1$_{max}$ fits substantially with the third calibration curve within a pre-defined confidence interval, the reader 30 preferably indicates that the chemical of interest is present. In one embodiment, the reader 30 indicates the presence of the chemical of interest by signaling an alarm 32. The third calibration curve is preferably generated from data resulting from directly testing the first reactive component 18 in the presence of the chemical of interest.

A specific example of a sensor configuration for sensor 10 includes the use of lithium oxide ($Li_2O$) as the first reactive component (or a portion of the first reactive component) as a "getter" for moisture ($H_2O$). For example, one mole of lithium oxide will react with one mole of water at approximately 25° C. resulting in an exothermic reaction that yields two moles of lithium hydroxide (LiOH). Other thermodynamic data for this particular reaction at different temperatures is given in Table 2 below. Because the thermodynamic data for this particular reaction (and many other reactions for many other chemical species) are known, the temperature change caused by such a reaction is known and may be used to identify whether water (or some other reactant) is in fact reacting with the first reactive component (e.g., lithium oxide). More specifically (using the example of $Li_2O$ and water), if water is present in the system, T1$_{max}$ should correlate directly with the anticipated difference between $\Delta T_{E1}$ and $\Delta T_R$ according to the third calibration curve, wherein the third calibration curve is generated based on thermodynamic data similar to that found in Table 2. Although the example given above may be used to determine the presence of one specific chemical species of interest, other embodiments using a first reactive component including only a single reactive species are contemplated that are selective to multiple chemical species (e.g., species in a particular range such as a<$T_{max}$<b, wherein "a" represents the lower boundary of the range and "b" represents the upper boundary of the range). An example may include a first reactive component that reacts with more than one chemical of interest, thereby potentially exhibiting a plurality of $T_{max}$ values correlating, respectively, to a plurality of chemicals of interest.

TABLE 2

| T (° C.) | ΔH (KJ) | ΔS (J/Kelvin) | ΔG (KJ) | K | Log(K) |
|---|---|---|---|---|---|
| 0 | −79.278 | 2.872 | −80.063 | 2.050E+15 | 15.312 |
| 25 | −86.090 | −21.940 | −79.549 | 8.665E+13 | 13.938 |
| 50 | −86.869 | −24.450 | −78.968 | 5.829E+12 | 12.766 |
| 75 | −87.610 | −26.658 | −78.329 | 5.662E+11 | 11.753 |
| 100 | −88.308 | −28.595 | −77.637 | 7.393E+10 | 10.869 |
| 125 | −88.967 | −30.306 | −76.901 | 1.229E+10 | 10.090 |
| 150 | −89.595 | −31.837 | −76.124 | 2.498E+09 | 9.398 |
| 175 | −90.204 | −33.234 | −75.310 | 6.006E+08 | 8.779 |

With reference to the Type J thermocouple example above, experimental data has shown that, at or about 20 degrees Centigrade, the ratio of volts to degrees Centigrade is $51 \times 10^{-6}$ volts per degree Centigrade or 51 microvolts per degree centigrade ($\mu V/° C.$). Thus, in order for a sensor associated with a Type J thermocouple to detect a change of $1 \times 10^{-1} °$ C., the sensor must be capable of a resolution of approximately 5.1 μV. For a Type R thermocouple, for example, the ratio of volts to degrees Centigrade is 7 $\mu V/° C$. Thus, in order for a sensor associated with a Type R thermocouple to detect a change of $1 \times 10^{-1} °$ C., the sensor must be capable of a resolution of approximately $7 \times 10^{-1}$ μV. When high resolution is necessary, the opportunity for interference or "background noise" to creep into the system is significant.

Figure 2:
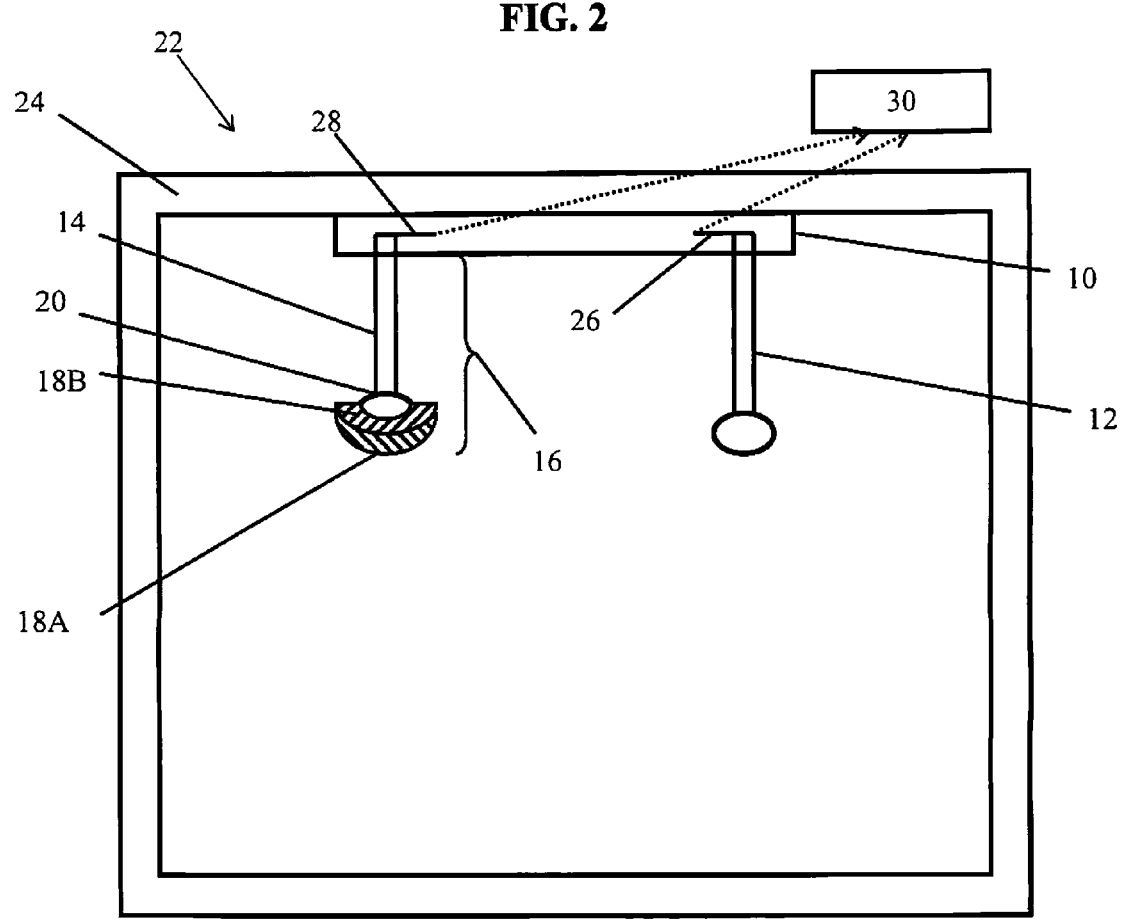
FIG. 2 shows a somewhat schematic side view of a related embodiment of a chemical sensor in a system.

A preferred embodiment of the disclosure avoids many of the issues associated with background noise. In this embodiment as shown in FIG. 2, the first reactive component 18 includes a first chemical substance 18A and a second chemical substance 18B. The first chemical substance 18A yields a product when exposed to the chemical of interest during the first chemical reaction. The product then reacts with the second chemical substance 18B through a second chemical reaction. The second chemical reaction causes a second maximum temperature variation $T2_{max}$ wherein $T2_{max}$ is greater than $T1_{max}$. By including the second chemical substance 18B in the first reactive component 18 and causing the variation between $\Delta V_{E1}$ and $\Delta V_R$ to increase, the sensor is more readily able to resolve such variation and thereby more accurately indicate the variation between $\Delta T_{E1}$ and $\Delta T_R$. With a more precise determination of the variation between $\Delta T_{E1}$ and $\Delta T_R$, the sensor is better able to precisely determine the variation between $T2_{max}$ and $T1_{max}$, thereby providing information regarding whether the chemical of interest is present. If the second chemical substance 18B were not included in the first reactive component of this embodiment, the chemical of interest may be more difficult or impossible to detect because of the relatively small magnitude of the variation between $\Delta V_{E1}$ and $\Delta V_R$ after the first chemical reaction but before the second chemical reaction.

In another embodiment, the reader 30 is configured for time stamping multiple measurements of $\Delta V_{E1}$ and $\Delta V_R$, thereby providing time stamped recorded values for $\Delta T_{E1}$ and $\Delta T_R$ based on the first calibration curve and the second calibration curve. First chemical reaction data may then be generated based on the time stamped values of $\Delta T_{E1}$ and $\Delta T_R$. The first chemical reaction data may include, for example, time plots that indicate reaction kinetics associated with the first chemical reaction including the duration of the first chemical reaction. Additionally, the first chemical reaction data may be analyzed to calculate the amount (e.g., concentration) of the chemical of interest detected in the system or any other calculations of interest that may be based in whole or in part on the first chemical reaction data. Second chemical reaction data may also be generated based on the time stamped values of $\Delta T_{E1}$ and $\Delta T_R$ and analyzed in a similar manner to the first chemical reaction data.

Figure 3:
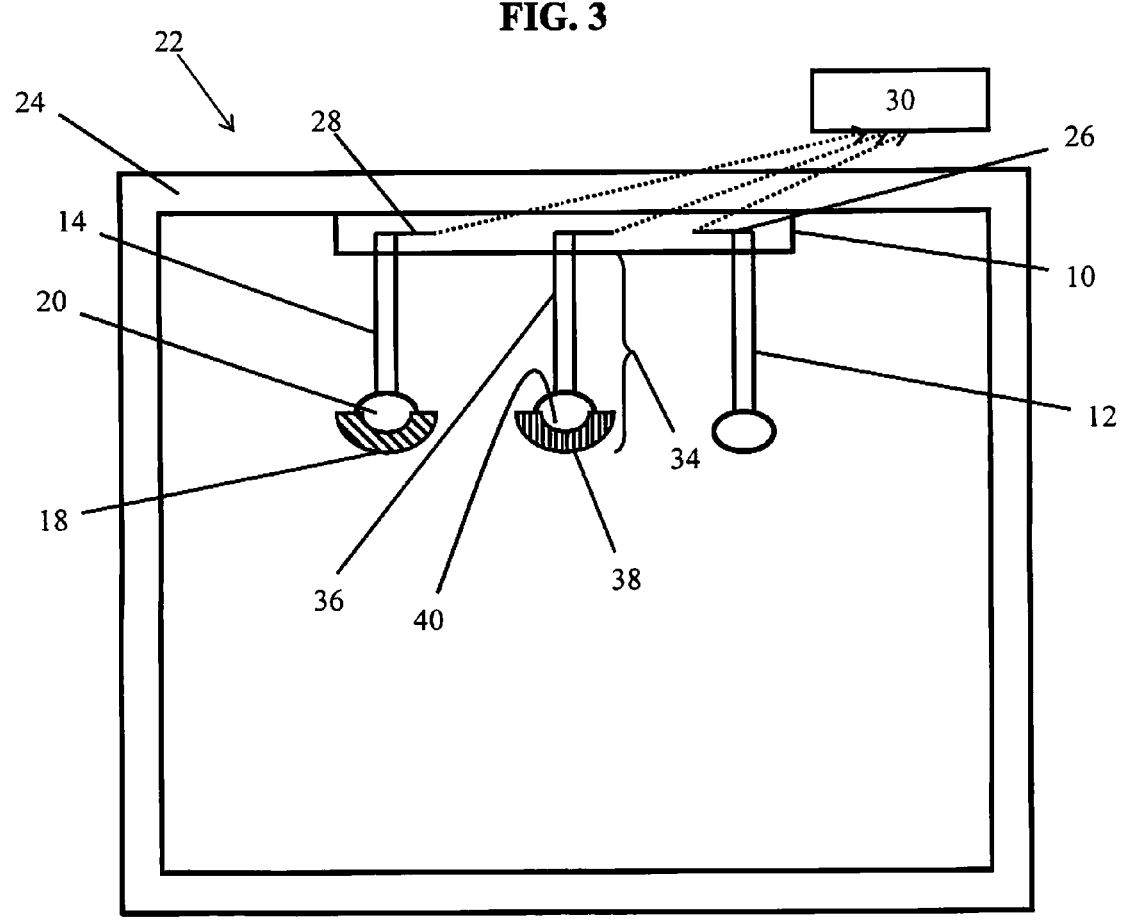
FIG. 3 shows a somewhat schematic side view of another related embodiment of a chemical sensor in a system.

The conductive heat transfer effects, if any, of the first reactive component 18 on the first joint 20 are preferably accounted for by including a calibration assembly 34 with the sensor 10 as shown in FIG. 3. The calibration assembly 34 includes a second experimental thermocouple 36 adjacent the reference thermocouple 12. During sensor 10 operation, the second experimental thermocouple 36 yields a slight voltage variation ($\Delta V_{E2}$) which corresponds to a temperature variation ($\Delta T_{E2}$) according to a fourth calibration curve. The fourth calibration curve is preferably substantially identical to the first calibration curve. A first non-reactive component 38 is attached proximate to the second experimental thermocouple 36 at a second joint 40. The first non-reactive component 38 is selected to substantially imitate the heat transfer properties of the first reactive component 18 so that any measurable difference between $\Delta T_{E2}$ and $\Delta T_R$ may be attributed to the presence of the first non-reactive component 38 proximate to the second joint 40. Because the first non-reactive component 38 substantially imitates the heat transfer properties of the first reactive component 18, the variation between the measured $\Delta V_{E2}$ and $\Delta V_R$ may be used to calibrate the reader 30 and/or the first experimental thermocouple 14 by subtracting the difference between $\Delta T_{E2}$ and $\Delta T_R$ from the calculated value of $T1_{max}$ and/or the time stamped differences between $\Delta T_{E1}$ and $\Delta T_R$.

Figure 4:
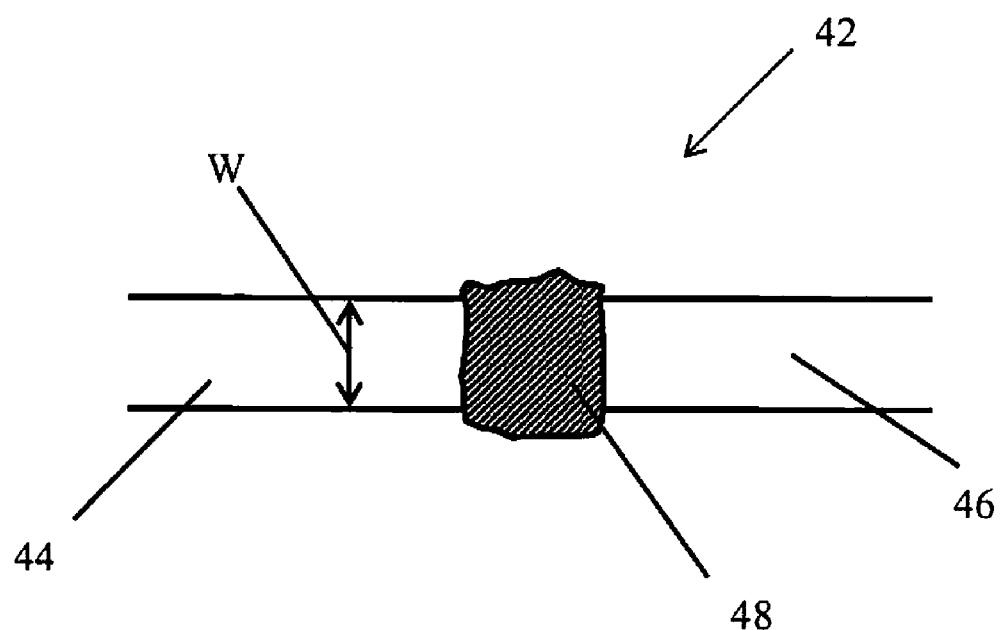
FIG. 4 shows a somewhat schematic side view of an embodiment of a thermocouple joint.

FIG. 4 shows a close-up view of an embodiment of a modified experimental thermocouple 42 including a first modified experimental thermocouple lead 44 and a second modified experimental thermocouple lead 46 attached together along an experimental thermocouple joint 48. The aspect ratio of the experimental thermocouple joint preferably ranges from about 1.0 to about 1.5, although the aspect ratio could be broader in other embodiments. In one embodiment, the width "W" of the leads ranges from about $3 \times 10^{-3}$ inches to about $5 \times 10^{-3}$ inches and is most preferably about $3 \times 10^{-3}$ inches. An embodiment of a chemical sensor may include, for example, the modified experimental thermocouple 42 oriented adjacent a similarly structured reference thermocouple to operate in a fashion similar to embodiments of the chemical sensor 10 discussed above.

Figure 5:
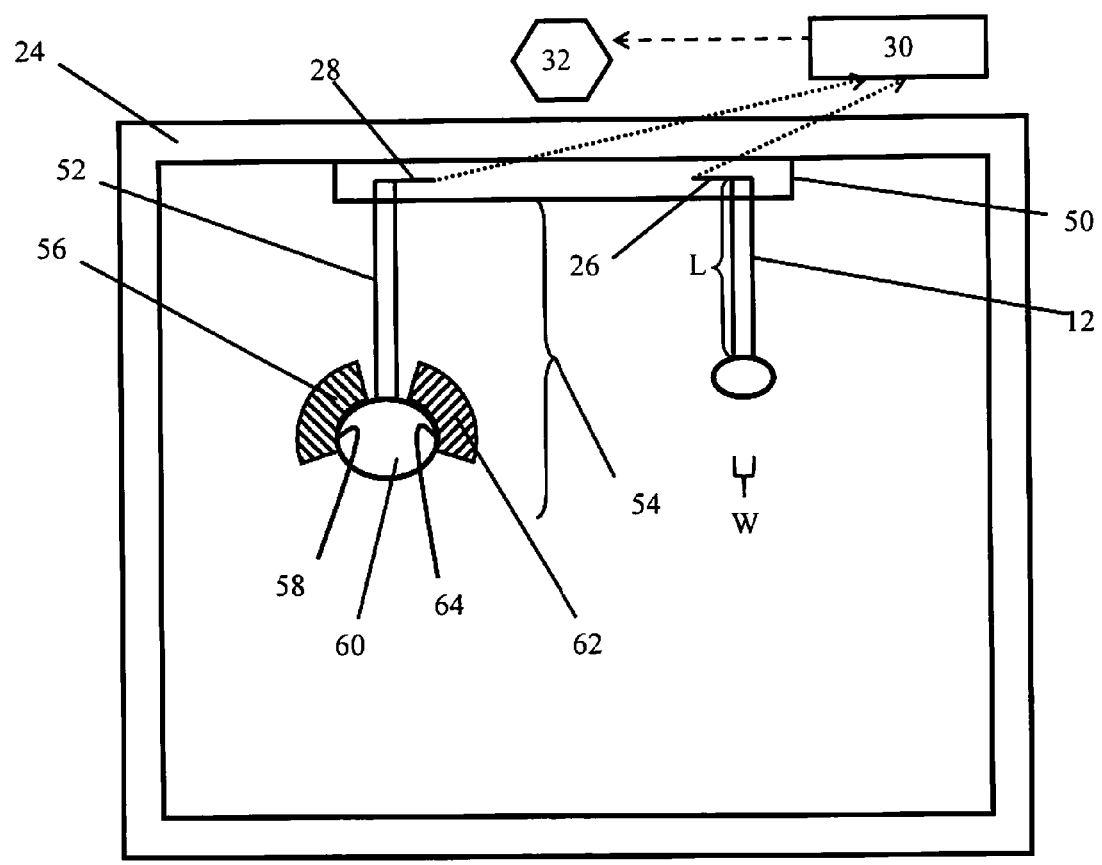
FIG. 5 shows a somewhat schematic side view of another related embodiment of a chemical sensor in a system.

In yet another embodiment shown in FIG. 5, a chemical sensor 50 includes a reference thermocouple 12 and a first experimental thermocouple 52 adjacent the reference thermocouple 12. The first experimental thermocouple 52 forms part of a first detector assembly 54 including the first experimental thermocouple 52, a first reactive component 56 attached proximate a first surface 58 of a joint 60 along the first experimental thermocouple 54, and a second reactive component 62 attached proximate a second surface 64 of the joint 60. The variation in an electric property (e.g., voltage) across the joint 60 is attributable to one of four basic events (excluding the possibility of apparatus malfunction) including (a) a reaction between the first reactive component 56 and a first reactant of interest, (b) a reaction between the second reactive component 62 and a second reactant of interest, (c) the simultaneous reaction between the first reactive component 56 and the first reactant of interest and a reaction between the second reactive component 62 and the second reactant of interest, or (d) a reaction between the first reactive component 56 and the second reactive component 62. Because the identities of the first reactive component 56 and the second component 62 are known, the properties (e.g., thermodynamic empirical data and reaction kinetics data) of these components are known or calculable. Therefore, the components may be (and preferably are) selected so that event (d) does not occur in any significant amount. Moreover, indicia corresponding to different absolute quantitative measurements of variation in an electric property produced along the joint 60 may be categorized as being associated with one of the three events described above (i.e., (a), (b), or (c)).

Figure 6:
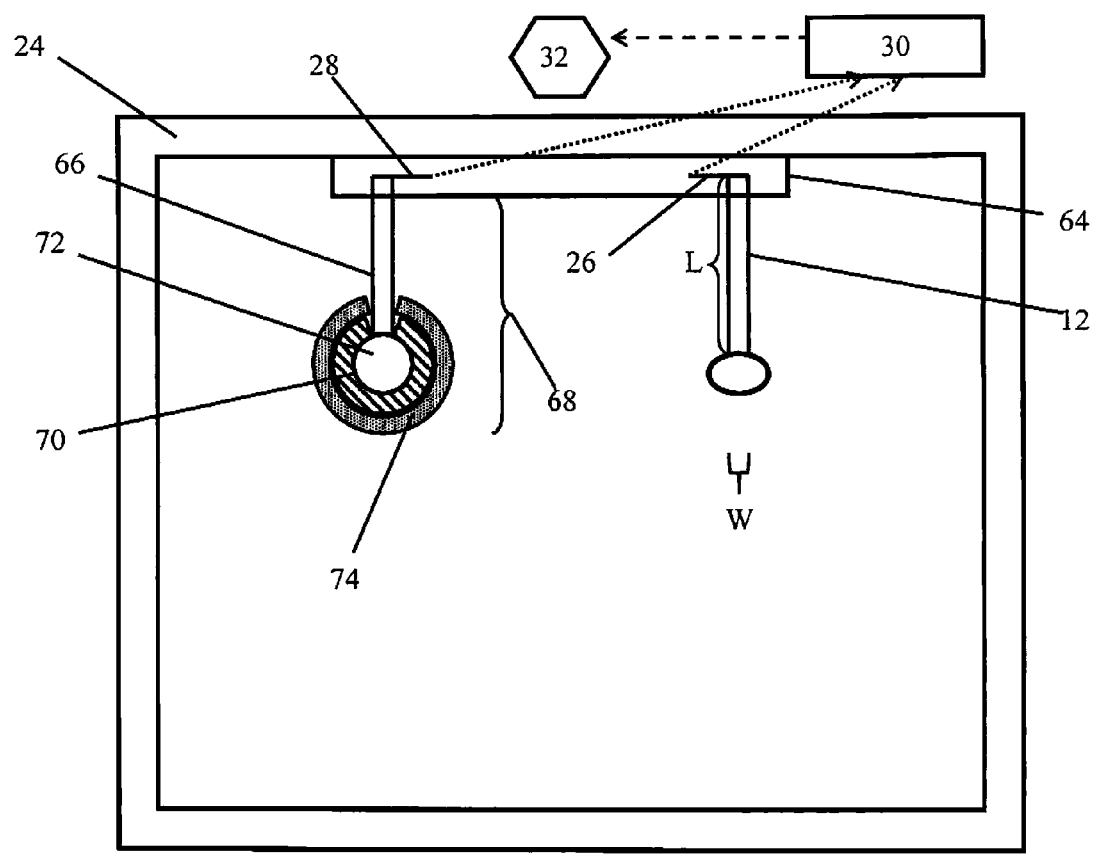
FIG. 6 shows a somewhat schematic side view of another related embodiment of a chemical sensor in a system in which a selective barrier is shown.

Another embodiment shown in FIG. 6 includes a chemical sensor 64 that further includes a reference thermocouple 12 and a first experimental thermocouple 66 adjacent the reference thermocouple 12. The first experimental thermocouple 66 forms part of a first detector assembly 68 including the first experimental thermocouple 66, a first reactive component 70 attached proximate a joint 72 located along the first experimental thermocouple 66, and a selective barrier 74 (e.g., a semi-permeable membrane) attached adjacent the first reactive component 70, thereby only allowing selected materials to contact and react with the first reactive component 70. The selective barrier 74 may include any semi-permeable membrane or other chemical or physical barrier known to a person having ordinary skill in the art. In a related embodiment, the selective barrier 74 may substantially cover the entire exposed area of the first experimental thermocouple 66 including any reactive component thereon. The latter embodiment may be useful in applications where undesirable reactants are present that could corrode or otherwise interfere with the performance of the first experimental thermocouple 66.

The disclosure also includes embodiments of a method for assessing a chemical of interest in a system. The term "assessing" (and other forms of this term) are to be understood as including the act of detecting, quantifying, and/or analyzing. In a first embodiment shown in FIG. 7, the method includes a step of measuring a first electrical property value based on the conditions at a reference location within the system (Step 110). An example includes sensor 10 measuring $\Delta V_R$ at the reference thermocouple 12. Another step includes triggering a first chemical reaction by exposing a reactive material to a chemical of interest at an experimental location inside the system (Step 112). An example of this step includes using sensor 10 to detect a chemical of interest such that a first chemical reaction is triggered when the first reactive component 18 begins to react with the chemical of interest. An additional step includes measuring a second electrical property value based on the conditions at the experimental location within the system (Step 114). An example of this step includes measuring $\Delta V_{E1}$ at the first experimental thermocouple 14. Yet another step includes comparing the measurement of the first electrical property value (e.g., $\Delta V_R$) with the measurement of the second electrical property value (e.g., $\Delta V_{E1}$) (Step 116). Step 116 may be carried out, for example, by the reader 30. Another step in this embodiment includes identifying the chemical of interest based on calibration data (e.g., the first calibration curve, the second calibration curve, and the third calibration curve) and the comparison of the measurement of the first electrical property value (e.g., $\Delta V_R$) with the measurement of the second electrical property value (e.g., $\Delta V_{E1}$) (Step 118).

Figure 7:
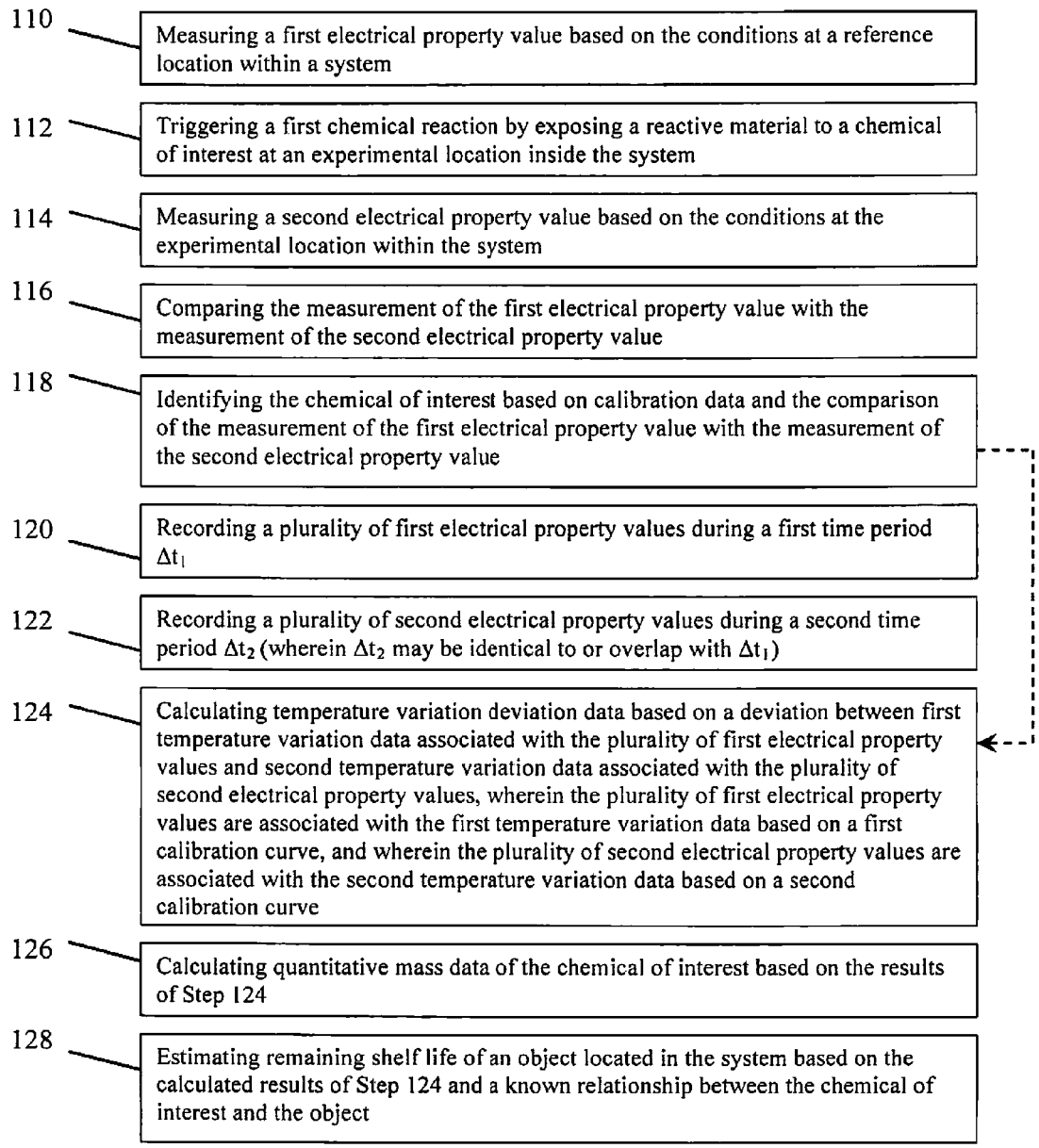
FIG. 7 shows a diagram of an embodiment of a method for detecting, quantifying, and/or analyzing a chemical of interest.

In a related embodiment shown further in FIG. 7, the method described above further includes a step of recording a plurality of first electrical property values during a first time period $\Delta t_1$ (Step 120). These and other recordings could be made, for example, by the reader 30, and the reader 30 could correlate measured voltage values to time using a chronometric device either built into the reader 30 or operatively attached to the reader 30. The embodiment may include a further step of recording a plurality of second electrical property values during a second time period $\Delta t_2$ (Step 122). In a preferred embodiment, $\Delta t_1$ is substantially identical to $\Delta t_2$.

In yet another embodiment further shown in FIG. 7, the embodiments described above, whether including Step 120 and 122 or not, may further include a step of calculating temperature variation deviation data based on a deviation between first temperature variation data associated with the plurality of first electrical property values and second temperature variation data associated with the plurality of second electrical property values, wherein the plurality of first electrical property values are associated with the first temperature variation data based on a first calibration curve, and wherein the plurality of second electrical property values are associated with the second temperature variation data based on a second calibration curve (Step 124). For example, a plurality of values similar to $T1_{max}$ could be calculated by the reader 30 based on a corresponding plurality of time stamped values of $\Delta V_R$ and $\Delta V_{E1}$ as described above. This data could then be plotted or otherwise used to calculate thermal excursion data during $\Delta t_1$ and $\Delta t_2$.

Another embodiment includes the additional step of calculating quantitative mass data of the chemical of interest (Step 126) based on the results from Step 124.

In a related embodiment, a method including at least steps 110, 112, 114, 116, 118, and 124 further includes a step of estimating remaining shelf life of an object located in the system based on the calculated results of Step 124 and a known relationship between the chemical of interest and the object (Step 128). For example, if components of a system are known to fail (based on, e.g., empirical data) after a specific amount (e.g., mass) of exposure to a chemical of interest, shelf life may be estimated by certain embodiments of the sensor 10 based on, for example, (1) rate of reaction data between the chemical of interest and the first reactive component 18 determined by the sensor 10 and (2) quantitative mass data of the chemical of interest determined by the sensor 10.

The disclosure further includes an embodiment of a method of assessing a chemical of interest in a system using chemical sensor 10, the method including the steps shown in FIG. 8 as follows: measuring a first electrical property based on the conditions at a first thermocouple (Step 210); exposing a first reactive component to a chemical of interest at a second thermocouple (Step 212); measuring a second electrical property based on the conditions at the second thermocouple during a thermal excursion at the second thermocouple caused by a first chemical reaction (Step 214); comparing the measurement of the first electrical property with the measurement of the second electrical property value (Step 216); and identifying the chemical of interest based on calibration data and the comparison of the measurement of the first electrical property with the measurement of the second electrical property (Step 218).

The disclosure also includes an embodiment of a method for identifying a reaction temperature for a chemical of interest in a system. The method, shown in FIG. 9, includes a step of measuring a plurality of first electrical property values based on the conditions at a reference location within the system (Step 310). Additional steps include exposing a reactive material to a chemical of interest at an experimental location inside the system (Step 312); measuring a plurality of second electrical property values based on the conditions at the experimental location within the system (Step 314); comparing the measured plurality of first electrical property values with the plurality of second electrical property values (Step 316); measuring the temperature of the system adjacent the reference location and the experimental location (Step 318); and controlling the temperature of the system so that the measured temperature in the system remains substantially unchanged and is therefore known when measurements are taken of the plurality of first electrical property values and the plurality of second electrical property values (Step 320). The term "exposing" as used with regard to Step 312 and elsewhere herein is hereby defined to include either passive or active exposure, or both. "Passive" exposure may be broadly understood as merely placing a reactive material in a particular place. "Active" exposure, on the other hand, is to be understood as doing more than merely placing a reactive material in a particular place such as, for example, introducing a catalyst directly to or near the reactive component so that the reactive component is more or less likely to react and/or, for example, altering the temperature of the reactive component and/or its surroundings.

The method for identifying a reaction temperature for a chemical of interest in a system may be accomplished using the sensor 10. The comparing step described in Step 316 may be accomplished, for example, using the reader 30 described above or any other similar device known to a person having ordinary skill in the art. With regard to Step 318, the temperature of the system may be controlled by a thermostat or other temperature control device known to a person having ordinary skill in the art. The temperature control device or other associated device (e.g., reader 30) may also be configured to record the temperature of the system at regular intervals or based on one or more specific recording signals. The temperature control device (e.g., thermostat or reader 30) may be configured for generating, sending, or receiving a recording signal so that the temperature of the system (e.g., system 22) is at least recorded substantially when a chemical reaction begins between the reactive material (e.g., the first reactive component 18) and the chemical of interest. Alternatively, if system temperature is recorded on a regular basis within the system, the time substantially when a chemical reaction begins between the reactive material and the chemical of interest may be calculated by interpolation or other technique based on the recorded time data, temperature data, and/or any other applicable data (e.g., voltage data).

In summary, embodiments are disclosed herein for various chemical detection sensors and/or systems. The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A chemical sensor for assessing a chemical of interest in a system having an operational temperature that varies over a temperature range, the sensor comprising:
   a first thermocouple disposed in the system and configured for exhibiting a first electrical property that varies over the temperature range according to a first calibration curve;
   a first detector assembly comprising a second thermocouple and a proximate first reactive component, the first detector assembly disposed adjacent the first thermocouple in the system and wherein the second thermocouple is configured for exhibiting a second electrical property that varies over the temperature range according to a second calibration curve, and wherein the first reactive component undergoes a first chemical reaction correlating to a first maximum temperature variation if the first reactive component is exposed to a first chemical of interest, and wherein the second electrical property changes according to a temperature change caused by the first chemical reaction.

2. The chemical sensor of claim 1 further comprising:
   a reader configured to compare the first electrical property and the second electrical property, to use the first calibration curve and the second calibration curve to calculate a first maximum temperature property variation between the first thermocouple and the second thermocouple wherein the first maximum temperature property variation varies according to a third calibration curve associated with the chemical of interest, and to use the first maximum temperature property variation between the first thermocouple and the second thermocouple along with the third calibration curve to indicate the presence of the first chemical of interest.

3. The chemical sensor of claim 2 wherein the reader is further configured for recording time stamped temperature property data for the first thermocouple and the second thermocouple.

4. The chemical sensor of claim 3 wherein the reader is further configured for using the time stamped temperature property data to generate first chemical reaction data based on the time stamped temperature property data associated with the first chemical reaction.

5. The chemical sensor of claim 4 wherein the reader is further configured for analyzing the first chemical reaction data according to an analysis program and generating output data based on an analysis of the first chemical reaction data.

6. The chemical sensor of claim 2 further comprising:
   a calibration assembly comprising a third thermocouple adjacent the first thermocouple and a first non-reactive component proximate the third thermocouple, the third thermocouple configured for generating a third electrical property that varies over the temperature range, wherein the first non-reactive component is selected so as to substantially imitate the conductive heat transfer properties of the first reactive component, wherein the variation of the third electrical property may be compared by the reader to the variation of the first electrical property, and wherein the effect of any difference between the variation of the first electrical property and the variation of the third electrical property may be accounted for during the calculation of the first maximum temperature property variation.

7. The chemical sensor of claim 2 further comprising:
   a second detector assembly comprising a third thermocouple and a proximate second reactive component, the second detector assembly disposed adjacent the first thermocouple in the system and wherein the third thermocouple is configured for generating a third electrical property that varies over the temperature range according to a third calibration curve, and wherein the second reactive component undergoes a second chemical reaction if the second reactive component is exposed to a second chemical of interest, and wherein the third electrical property changes according to a temperature change induced by the second chemical reaction, the reader configured to compare the first electrical property and the third electrical property, to use the first calibration curve and the third calibration curve to calculate a second maximum temperature property variation between the first thermocouple and the third thermocouple wherein the second maximum temperature property variation varies according to a fourth calibration curve, and to use the second maximum temperature property variation between the first thermocouple and the third thermocouple along with the fourth calibration curve to indicate the presence of the second chemical of interest.

8. The chemical sensor of claim 1 wherein the first reactive component comprises a first chemical substance that yields a product when exposed to the chemical of interest during the first chemical reaction and wherein the product reacts with a second chemical substance in the reactive component, defining a second chemical reaction correlating to a second maximum temperature property variation, wherein the magnitude of the second maximum temperature properly variation is greater than the magnitude of the first maximum temperature property variation.

9. The chemical sensor of claim 1 wherein the first reactive component is attached adjacent a first surface along the second thermocouple and wherein the first detector assembly further comprises a second reactive component attached adjacent a second surface along the second thermocouple.

10. The chemical sensor of claim 1 wherein the second thermocouple further comprises a selective barrier attached adjacent the second thermocouple such that the first reactive component is substantially prevented from being exposed to chemicals that are substantially incapable of transporting through the selective barrier.

11. A closed system comprising an enclosed structure and the chemical sensor of claim 1 attached to the interior of the enclosed structure.

12. The closed system of claim 11 wherein the chemical of interest is selected from the group consisting of a gas, a liquid, a solid, and a combination thereof, and wherein the chemical of interest is maintained in a gas mixture inside the enclosed structure.

13. The chemical sensor of claim 1 further comprising:
a second detector assembly comprising a third thermocouple and a proximate second reactive component, the second detector assembly disposed adjacent the first thermocouple in the system and wherein the third thermocouple is configured for generating a third electrical property that varies over the temperature range according to a third calibration curve, and wherein the second reactive component undergoes a second chemical reaction if the second reactive component is exposed to a second chemical of interest, and wherein the third electrical property changes according to a temperature change induced by the second chemical reaction.

14. A method for assessing a chemical of interest in a system using the chemical sensor of claim 1, the method comprising the steps of
a. measuring the first electrical property based on the conditions at the first thermocouple;
b. exposing the first reactive component to the chemical of interest at the second thermocouple;
c. measuring the second electrical property based on the conditions at the second thermocouple during a thermal excursion at the second thermocouple caused by the first chemical reaction;
d. comparing the measurement of the first electrical property with the measurement of the second electrical property value; and
e. identifying the chemical of interest based on calibration data and the comparison of the measurement of the first electrical property with the measurement of the second electrical property.

15. The chemical sensor of claim 1 wherein the temperature range over which the operational temperature of the chemical sensor varies ranges at least about 25° C. in maximum fluctuation during chemical sensor operation.

16. The chemical sensor of claim 1 wherein the temperature range over which the operational temperature of the chemical sensor varies ranges from at least about 0° C. to at least about 125° C.

17. The chemical sensor of claim 1 for assessing a chemical of interest in a system having an operational temperature that varies over a temperature range further comprising a chemical sensor for passively assessing the chemical of interest.

18. The chemical sensor of claim 1 further comprising the first reactive component wherein the first reactive component consists essentially of lithium oxide.

19. An open system comprising the chemical sensor of claim 1.

20. The open system of claim 19 wherein the chemical of interest is selected from the group consisting of a gas, a liquid, a solid, and a combination thereof, and wherein the chemical of interest is carried in a gas.

* * * * *

UNITED STATES PATENT AND TRADEMARK OFFICE
CERTIFICATE OF CORRECTION

| | | |
|---|---|---|
| PATENT NO. | : 8,114,677 B2 | |
| APPLICATION NO. | : 12/243247 | |
| DATED | : February 14, 2012 | |
| INVENTOR(S) | : Morrell et al. | |

It is certified that error appears in the above-identified patent and that said Letters Patent is hereby corrected as shown below:

IN THE DRAWINGS, Sheet 8 of 9, FIG. 8, the term --value-- should appear after each instance of the term "electrical property."

Column 1, line 65, the term --value-- should appear after the term "electrical property."

Column 2, lines 4, 10, 22, 23, 61, 65, and 66, the term --value-- should appear after each occurrence of the term "electrical property."

Column 3, lines 1, 2, 10, 15, 24, 28, and 31, the term --value-- should appear after each occurrence of the term "electrical property."

Column 5, line 46, the term --value-- should appear after the term "electrical property."

Column 8, line 55, the term --value-- should appear after the term "electric property."

Column 9, line 6, the term --value-- should appear after the term "electric property."

Column 10, lines 42, 46, 49, 53, and 54, the term --value-- should appear after each occurrence of the term "electrical property."

Column 11, Claim 1, line 62, the term --value-- should appear after the term "electrical property."

Column 12, Claim 1, lines 3 and 9, the term --value-- should appear after each occurrence of the term "property"; Claim 2, lines 12 and 13, the term --value-- should appear after each occurrence of the term "property"; Claim 6, lines 42, 46, 48, 49 and 50, the term --value-- should appear after each occurrence of the term "property"; and Claim 7, lines 59, 64, 66 and 67, the term --value-- should appear after each occurrence of the term "property."

Signed and Sealed this
Twenty-sixth Day of June, 2012

David J. Kappos
*Director of the United States Patent and Trademark Office*

Column 13, line 18, the term "properly variation" should read "property variation"; and claim 13, line 47, the term --value-- should appear after the term "property."

Column 14, Claim 13, line 5, the term --value-- should appear after the term "property"; and Claim 14, lines 10, 14, 19, 20, 23 and 24, the term --value-- should appear after each occurrence of the term "property."